United States Patent
Cole et al.

(10) Patent No.: US 10,434,247 B2
(45) Date of Patent: *Oct. 8, 2019

(54) CATHETER INSERTION DEVICE

(71) Applicant: Becton, Dickinson and Company, Franklin Lakes, NJ (US)

(72) Inventors: Russell Cole, River Vale, NJ (US); Michael Creighton, Hatboro, NJ (US); Arthur Klotz, Willow Grove, PA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 193 days.

This patent is subject to a terminal disclaimer.

(21) Appl. No.: 15/301,076

(22) PCT Filed: Apr. 23, 2015

(86) PCT No.: PCT/US2015/027365
§ 371 (c)(1),
(2) Date: Sep. 30, 2016

(87) PCT Pub. No.: WO2015/164651
PCT Pub. Date: Oct. 29, 2015

(65) Prior Publication Data
US 2017/0119959 A1  May 4, 2017

Related U.S. Application Data

(60) Provisional application No. 61/983,983, filed on Apr. 24, 2014.

(51) Int. Cl.
*A61M 5/142* (2006.01)
*A61M 5/168* (2006.01)

(52) U.S. Cl.
CPC .............. *A61M 5/14248* (2013.01); *A61M 2005/14252* (2013.01); *A61M 2005/16863* (2013.01)

(58) Field of Classification Search
CPC .............. A61M 5/14248; A61M 5/158; A61M 2005/1585; A61M 2025/028
See application file for complete search history.

(56) References Cited

U.S. PATENT DOCUMENTS 5,312,364 A * 5/1994 Jacobs ............... A61B 17/3472
604/174
6,293,925 B1  9/2001 Safabash et al.
(Continued)

FOREIGN PATENT DOCUMENTS

| JP | 2007510499 A | 4/2007 |
| JP | 2014507227 A | 3/2014 |
| WO | WO-2009039013 A1 | 3/2009 |

OTHER PUBLICATIONS

International Search Report and Written Opinion dated Jul. 28, 2015 issued in the corresponding PCT Patent Application No. PCT/US2015/027365.

(Continued)

*Primary Examiner* — Bhisma Mehta
*Assistant Examiner* — William R Frehe
(74) *Attorney, Agent, or Firm* — Dickinson Wright PLLC

(57) ABSTRACT

A catheter insertion device (18) includes a housing (12) with a base (14), a catheter (28), an introducer needle (30) and an actuator (26) mounted within the housing. The catheter (28) and needle (30) are coupled to the actuator (26) and movable between a first position where the catheter and needle are retracted within the housing and a second position where the catheter and needle extend from the housing, and where the needle retracts into the actuator when the catheter and needle reach the second position. The actuator (26) has a detent (84) that engages a first recess (76) to require a predetermined force to depress the actuator (26) which is greater than the force necessary to slide the actuator (26) to the second (Continued)

position where the detent (84) engages a second recess (80) in the housing (12) to hold the actuator in the deployed position.

20 Claims, 10 Drawing Sheets

(56) References Cited

U.S. PATENT DOCUMENTS

| | | | |
|---|---|---|---|
| 7,909,791 B2 | 3/2011 | Liniger et al. | |
| 10,251,999 B2* | 4/2019 | Cole | A61M 5/158 |
| 2005/0101912 A1* | 5/2005 | Faust | A61M 5/158 |
| | | | 604/117 |
| 2006/0142698 A1 | 6/2006 | Ethelfeld | |
| 2008/0140014 A1* | 6/2008 | Miller | A61B 17/3472 |
| | | | 604/180 |
| 2009/0012472 A1 | 1/2009 | Ahm et al. | |
| 2009/0099521 A1 | 4/2009 | Gravesen et al. | |
| 2010/0049129 A1 | 2/2010 | Yokoi et al. | |
| 2012/0150123 A1 | 6/2012 | Lawrence et al. | |
| 2014/0058353 A1* | 2/2014 | Politis | A61M 5/14248 |
| | | | 604/506 |
| 2017/0028128 A1* | 2/2017 | Cole | A61M 5/158 |

OTHER PUBLICATIONS

Chinese Office Action dated Feb. 10, 2017 which issued in the corresponding Patent Application No. 201590000455.1.

Japanese Office Action dated Jan. 29, 2019, which issued in the corresponding Japanese Patent Application No. 2016-563966.

* cited by examiner

CATHETER INSERTION DEVICE

CROSS-REFERENCE TO RELATED APPLICATION

This application claims priority under 35 USC § 119(e) from U.S. Provisional Patent Application Ser. No. 61/983,983 filed on Apr. 24, 2014, the disclosure of which is incorporated herein by reference in its entirety.

FIELD OF THE INVENTION

The present invention is directed to a catheter insertion device for use in a patch pup or infusion set and to a method of inserting a catheter into a patient using the catheter insertion device. The invention is directed to a catheter insertion device for use with a patch pump, infusion set or other delivery device for introducing a catheter into a patient and automatically retracting an insertion needle once the catheter is moved to an extended position. The invention, in another embodiment, is directed to a manually operated catheter insertion device where a predetermined force is required to actuate the device to provide rapid penetration of the catheter into the patient.

BACKGROUND OF THE INVENTION

Diabetes is a group of diseases characterized by high levels of blood glucose resulting from the inability of diabetic patients to maintain proper levels of insulin production when required. Persons with diabetes will require some form of daily insulin therapy to maintain control of their glucose levels. Diabetes can be dangerous to the affected patient if it is not treated, and it can lead to serious health complications and premature death. However, such complications can be minimized by utilizing one or more treatment options to help control the diabetes and reduce the risk of complications.

The treatment options for diabetic patients include specialized diets, oral medications and/or insulin therapy. The main goal of diabetes treatment is to control the diabetic patient's blood glucose or sugar level. However, maintaining proper diabetes management may be complicated because it has to be balanced with the activities of the diabetic patient.

For the treatment of type 1 diabetes, there are two principal methods of daily insulin therapy. In the first method, diabetic patients use syringes or insulin pens to self-inject insulin when needed. This method requires a needle stick for each injection, and the diabetic patient may require three to four injections daily. The syringes and insulin pens that are used to inject insulin are relatively simple to use and cost effective.

Another effective method for insulin therapy and managing diabetes is infusion therapy or infusion pump therapy in which an insulin pump is used. The insulin pump can provide continuous infusion of insulin to a diabetic patient at varying rates in order to more closely match the functions and behavior of a properly operating pancreas of a non-diabetic person that produces the required insulin, and the insulin pump can help the diabetic patient maintain his/her blood glucose level within target ranges based on the diabetic patient's individual needs.

Infusion pump therapy requires an infusion cannula, typically in the form of an infusion needle or a flexible catheter, that pierces the diabetic patient's skin and through which, infusion of insulin takes place. Infusion pump therapy offers the advantages of continuous infusion of insulin, precision dosing, and programmable delivery schedules.

In infusion therapy, insulin doses are typically administered at a basal rate and in a bolus dose. When insulin is administered at a basal rate, insulin is delivered continuously over 24 hours in order to maintain the diabetic patient's blood glucose levels in a consistent range between meals and rest, typically at nighttime. Insulin pumps may also be capable of programming the basal rate of insulin to vary according to the different times of the day and night. In contrast, a bolus dose is typically administered when a diabetic patient consumes a meal, and generally provides a single additional insulin injection to balance the consumed carbohydrates. Insulin pumps may be configured to enable the diabetic patient to program the volume of the bolus dose in accordance with the size or type of the meal that is consumed by the diabetic patient. In addition, insulin pumps may also be configured to enable the diabetic patient to infuse a correctional or supplemental bolus dose of insulin to compensate for a low blood glucose level at the time when the diabetic patient is calculating the bolus dose for a particular meal that is to be consumed.

Insulin pumps advantageously deliver insulin over time rather than in single injections, typically resulting in less variation within the blood glucose range that is recommended. In addition, insulin pumps may reduce the number of needle sticks which the diabetic patient must endure, and improve diabetes management to enhance the diabetic patient's quality of life.

Typically, regardless of whether a diabetic patient uses multiple direct injections (MDIs) or a pump, the diabetic patient takes fasting blood glucose medication (FBGM) upon awakening from sleep, and also tests for glucose in the blood during or after each meal to determine whether a correction dose is required. In addition, the diabetic patient may test for glucose in the blood prior to sleeping to determine whether a correction dose is required, for instance, after eating a snack before sleeping.

To facilitate infusion therapy, there are generally two types of insulin pumps, namely, conventional pumps and patch pumps. Conventional pumps require the use of a disposable component, typically referred to as an infusion set, tubing set or pump set, which conveys the insulin from a reservoir within the pump into the skin of the user. The infusion set consists of a pump connector, a length of tubing, and a hub or base from which a cannula, in the form of a hollow metal infusion needle or flexible plastic catheter extends. The base typically has an adhesive that retains the base on the skin surface during use. The cannula can be inserted onto the skin manually or with the aid of a manual or automatic insertion device. The insertion device may be a separate unit required by the user.

Another type of insulin pump is a patch pump. Unlike a conventional infusion pump and infusion set combination, a patch pump is an integrated device that combines most or all of the fluidic components, including the fluid reservoir, pumping mechanism and mechanism for automatically inserting the cannula, in a single housing which is adhesively attached to an infusion site on the patient's skin, and does not require the use of a separate infusion or tubing set. A patch pump containing insulin adheres to the skin and delivers the insulin over a period of time via an integrated subcutaneous cannula. Some patch pumps may wirelessly communicate with a separate controller device (as in one device sold by Insulet Corporation under the brand name OmniPod®), while others are completely self-contained.

Such devices are replaced on a frequent basis, such as every three days, when the insulin reservoir is exhausted or complications may otherwise occur, such as restriction in the cannula or the infusion site.

As patch pumps are designed to be a self-contained unit that is worn by the diabetic patient, it is preferable to be as small as possible so that it does not interfere with the activities of the user. Thus, in order to minimize discomfort to the user, it would be preferable to minimize the overall thickness of the patch pump. However, in order to minimize the thickness of the patch pump, its constituent parts should be reduced as much as possible. One such part is the insertion mechanism for automatically inserting the cannula into the user's skin.

In order to minimize the height of the insertion mechanism, some conventional insertion mechanisms are configured to insert the cannula at an acute angle from the surface of the skin, e.g. 30-45 degrees. However, it may be preferable to insert the cannula perpendicular or close to the perpendicular from the surface of the skin, since this would require the minimum length of cannula insertion. In other words, with the minimum length of cannula being inserted into the user's skin, the user can experience greater comfort and fewer complications, such as premature kinking of the cannula. But one problem with configuring the insertion mechanism to insert the cannula perpendicular to the surface of the skin is that this may increase the overall height of the insertion mechanism, and therefore of the patch pump itself.

The main problem with configuring the insertion mechanism to insert the cannula perpendicular to the surface of the skin is that this may likely increase the overall height of the insertion mechanism, and therefore the patch pump, itself. For instance, U.S. Pat. No. 7,909,791 discloses a stand-alone insertion device for infusion sets that utilize various linkages, gears and springs to automatically insert a cannula vertically or perpendicularly into the user's skin. However, incorporating such a device into a patch pump would not only add considerably bulk, complexity and cost, but would greatly increase the height of the patch pump.

Accordingly, a need exists for an improved insertion mechanism for use in a limited space environment, such as in the patch pump, that can cost-effectively insert a cannula vertically or close to perpendicularly into the surface of a user's skin, while minimizing or reducing its height, in order to reduce the overall height of the device the insertion mechanism is incorporated into, such as a patch pump.

SUMMARY OF THE INVENTION

The present invention is directed to a catheter insertion device for use with an infusion set or patch pump and to a method of inserting a catheter into a patient using the catheter insertion device. The invention in one embodiment is a catheter insertion device having an actuator that is manually depressed to insert the catheter by the use of an insertion needle or cannula into the patient and to automatically retract the insertion needle from the catheter. In another embodiment, the invention is an infusion set including the catheter insertion device.

One object of the invention is to provide a catheter insertion device or catheter introducing device in an infusion set.

Another object of the invention is to provide a catheter insertion device having a manually operated actuator that is pressed by the user to insert the catheter into the patient. The actuator is able to release the introducer needle when the catheter is moved to an extended position to retract the introducer needle automatically.

One embodiment of the invention provides a catheter insertion device having a manually operated actuator to actuate the catheter insertion device where a predetermined force is required to move the actuator from a first position where the catheter and insertion needle are in a retracted position. Once the actuator is moved from the first position, the actuator moves toward a second position with a lower resisting force than that required to move or be released from the first position thereby enabling rapid deployment and insertion of the catheter into the patient. The actuator according to one embodiment has a detent that engages a recess in a housing when the actuator is in a first position. The actuator is movable between the first position and a second position where a catheter and insertion needle coupled to the actuator move to a second extended position with respect to the housing. A predetermined force is applied to the actuator to separate the detent from the recess where the required force is greater than a force needed to move the actuator to the second position so that the catheter and insertion needle quickly penetrate the skin of a patient.

Another feature of the invention is to provide a catheter insertion device where a catheter and an insertion needle are movable between a first position and a second position. A catheter hub is coupled to an insertion needle carrier during movement to the second position where the needle carrier then separates from the catheter hub. A spring is provided to automatically retract the needle carrier and needle with respect to the catheter and catheter hub.

These and other aspects of the invention are basically attained by providing a catheter insertion device having a housing with a base, a catheter movable between a first retracted position and a second extended position with respect to the base, an introducer needle within the catheter and movable between a first retracted position and a second extended position with respect to the base, and an actuator for actuating the device. The actuator moves the catheter and needle between a first position where the catheter and needle are retracted within the housing and a second position where the catheter and needle extend from the housing, and where the needle retracts automatically into the actuator when the catheter and needle are moved to the second position.

The various aspects of the invention are also attained by providing a catheter insertion device comprising a housing with a base, a catheter, an introducer needle and an actuator. The catheter is movable between a first retracted position and a second extended position with respect to the base. The introducer needle is movable between a first retracted position and a second extended position with respect to the base. The needle is slidably received within the actuator where the actuator is movable between a first position where the catheter and needle are in the respective first positions within the housing, and a second position where the catheter and needle are in the respective second positions. A needle carrier can be releasably coupled to a distal end of the catheter. The needle carrier is uncoupled from the catheter when the actuator and catheter are moved to the respective second positions to retract the needle into the actuator.

The features of the invention are also provided by a catheter insertion device comprising a housing having a base, and actuator coupled to the base and being movable between a first position and a second extended position, a catheter hub within the actuator and a catheter coupled to the catheter hub and being movable between a first position disposed within the base and a second position extending from the base when the actuator is in the second position. A needle carrier is slidably received in the actuator and slidable between a first extended position with respect to the actuator and catheter holder, and a second retracted position where the needle carrier is releasably coupled to the catheter hub. An introducer needle is received in the catheter and is coupled to the needle carrier where the needle carrier, introducer needle and catheter are movable to the extended position by moving the actuator and where the needle carrier separates from the catheter hub when the catheter hub is at the second position to retract the needle carrier and introducer needle into the actuator.

These and other aspects of the invention will become apparent from the following detailed description of the invention which, taken in conjunction with the annexed drawings, show various embodiments of the invention.

BRIEF DESCRIPTION OF THE DRAWINGS

The various objects, advantages and novel features of the exemplary embodiments of the present invention will be more readily appreciated from the following detailed description when read in conjunction with the appended drawings, in which.

DETAILED DESCRIPTION OF THE EXEMPLARY EMBODIMENTS

Figure 1:
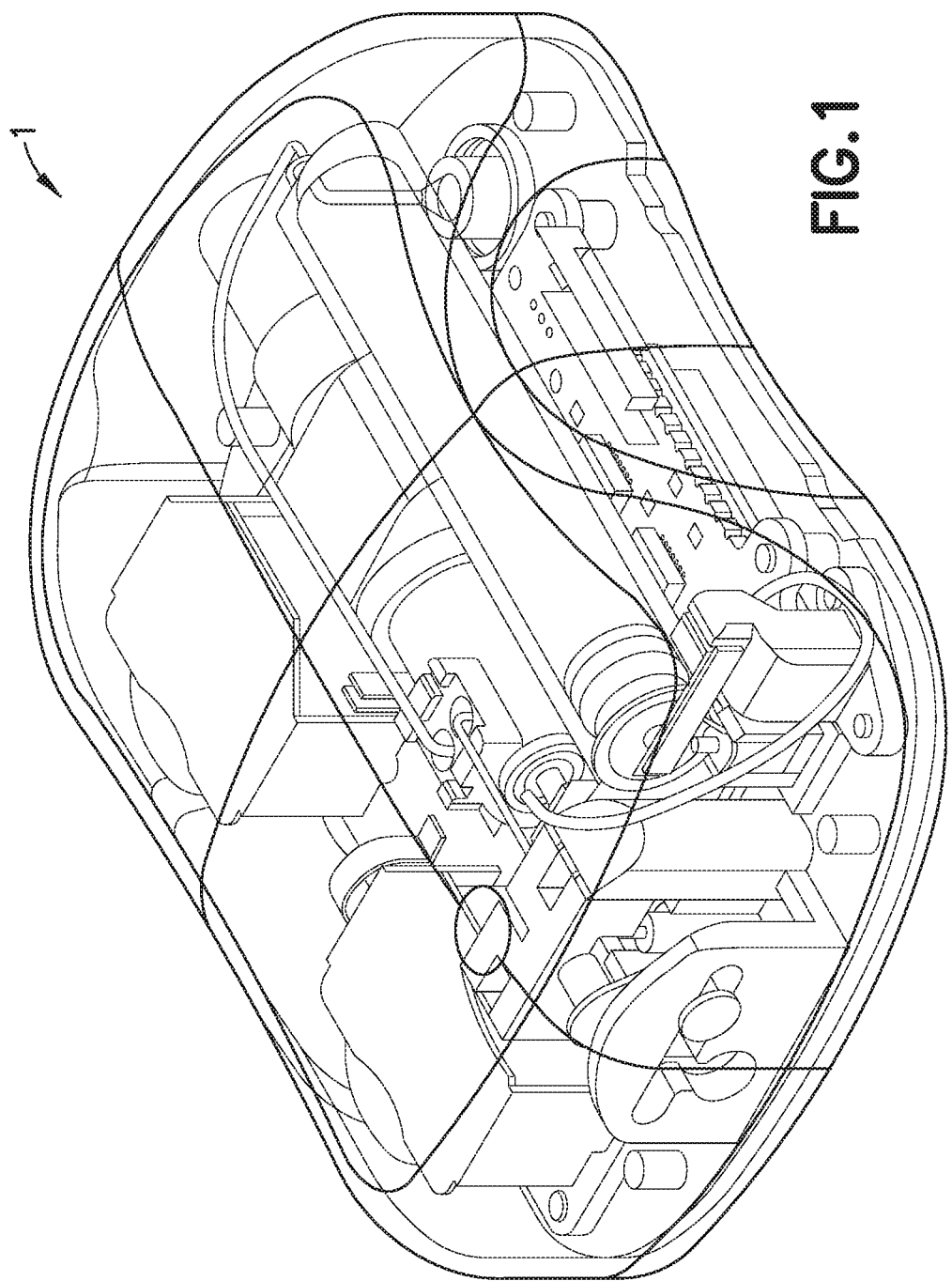
FIG. 1 is a perspective view of a patch pump incorporating a low-profile cannula insertion device.
Figure 2:
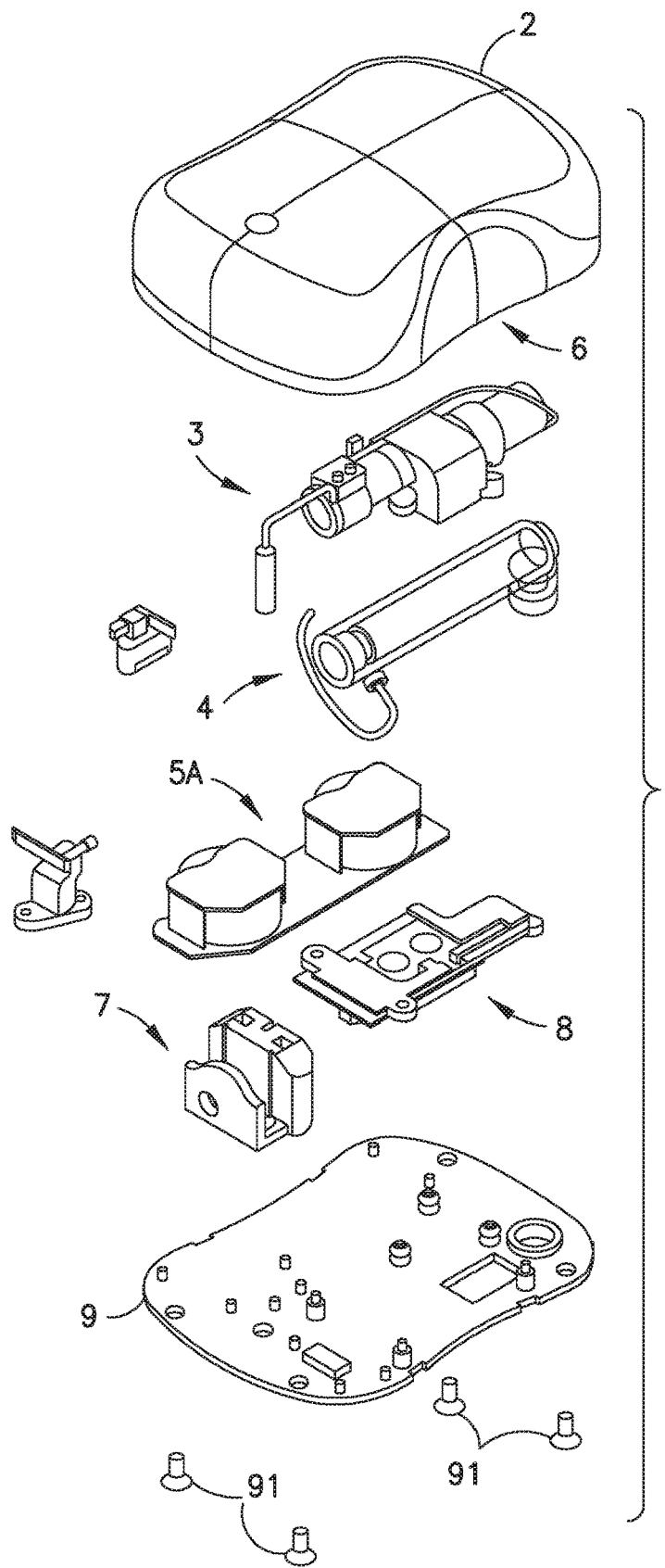
FIG. 2 is an exploded view of the various components of the patch pump of FIG. 1, illustrated with a cover.

FIG. 1 is a perspective view of an exemplary embodiment of a patch pump 1 according to an exemplary embodiment of the invention. The patch pump 1 is illustrated with a see-through cover for clarity and illustrates various components that are assembled to form the patch pump 1. FIG. 2 is an exploded view of the various components of the patch pump of FIG. 1, illustrated with a solid cover 2. The various components of the patch pump 1 may include: a reservoir 4 for storing insulin; a pump 3 for pumping insulin out of the reservoir 4; a power source 5 in the form of one or more batteries; an insertion mechanism 7 for inserting an inserter needle with a catheter into a user's skin; control electronics 8 in the form of a circuit board with optional communications capabilities to outside devices such as a remote controller and computer, including a smart phone; a dose button 6 on the cover 2 for actuating an insulin dose, including a bolus dose; and a base 9 to which various components above may be attached via fasteners 91. The patch pump 1 also includes various fluid connector lines that transfer insulin pumped out of the reservoir 4 to the infusion site.

It should be understood that inserter mechanisms come in various configurations. In some embodiments, the inserter mechanism inserts a soft catheter into the skin. In these embodiments, typically the soft catheter is supported on a rigid insertion needle. The insertion needle is inserted into the skin along with the soft catheter, and then retracted from the skin, leaving the soft catheter in the skin. In other embodiments, a soft catheter is not provided, and the insertion needle remains in the skin and forms a portion of the insulin flow path to deliver insulin until the infusion is finished. Insertion needles are typically hollow, and need to be hollow if they form part of the insulin flow path. However, insertion needles that support a soft catheter and then retract may be solid or hollow. If the insertion needle deploys a soft catheter, and retracts but remains part of the insulin flow path, then the insertion needle should be hollow. However, if the insertion needle deploys a soft catheter and then retracts but does not form part of the insulin flow path, then the insertion needle may be solid or hollow. In either case, the insertion needle is preferably rigid enough to reliably penetrate the skin, but otherwise may be made flexible enough to provide comfort to the user.

Figure 3:
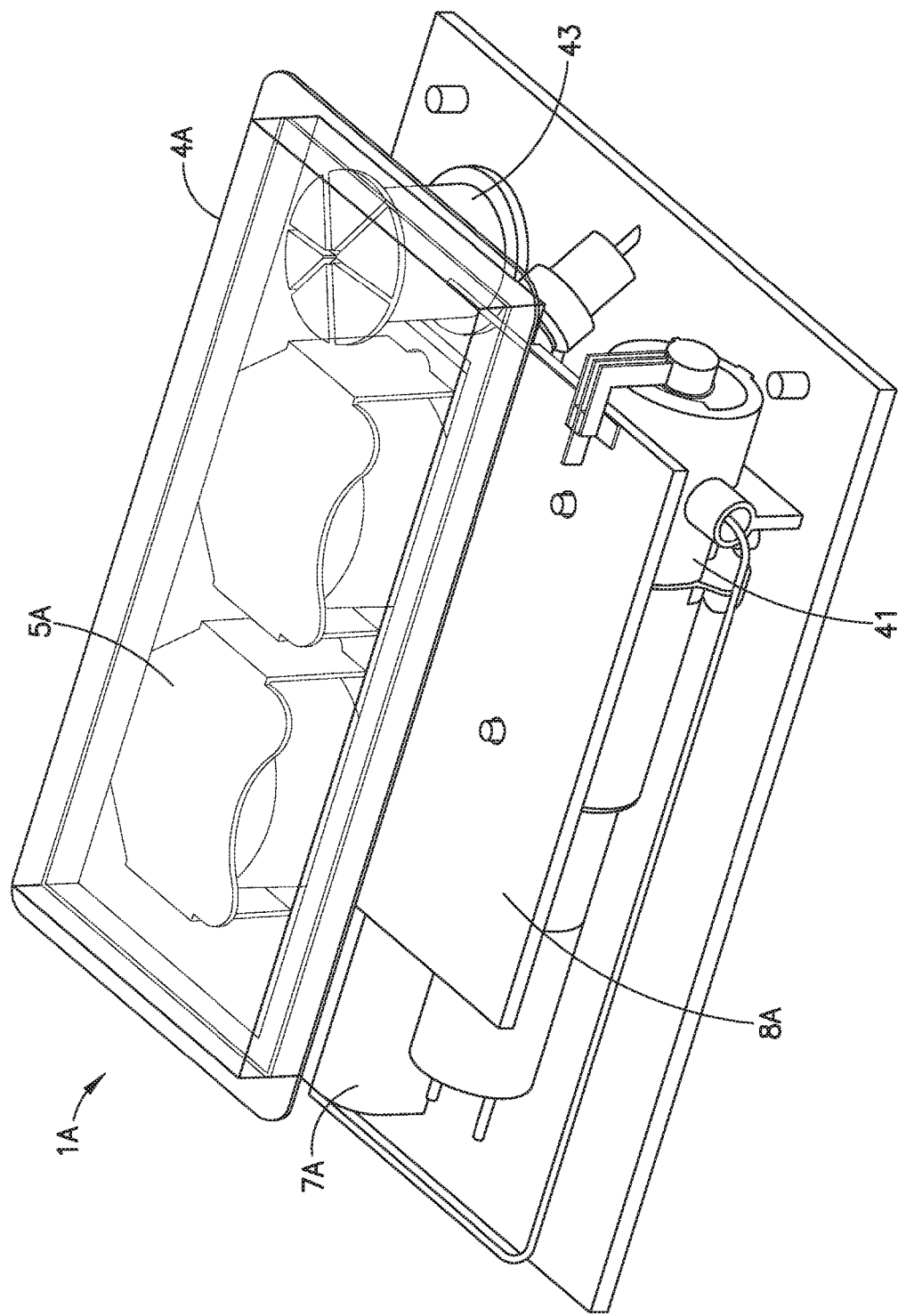
FIG. 3 is a perspective view of an alternative design for a patch pump having a flexible reservoir, illustrated without a cover.

FIG. 3 is a perspective view of an alternative design for a patch pump 1A having a flexible reservoir 4A, and illustrated without a cover. Such arrangement may further reduce the external dimensions of the patch pump 1A, with the flexible reservoir 4A filling voids within the patch pump 1A. The patch pump 1A is illustrated with a conventional cannula insertion device 7A that inserts the cannula, typically at an acute angle, less than 90 degrees, at the surface of a user's skin. The patch pump 1A further comprises: a power source 5A in the form of batteries; a metering sub-system 41 that monitors the volume of insulin and includes a low volume detecting ability; control electronics 8A for controlling the components of the device; and a reservoir fill port 43 for receiving a refill syringe 45 to fill the reservoir 4A.

Figure 4:
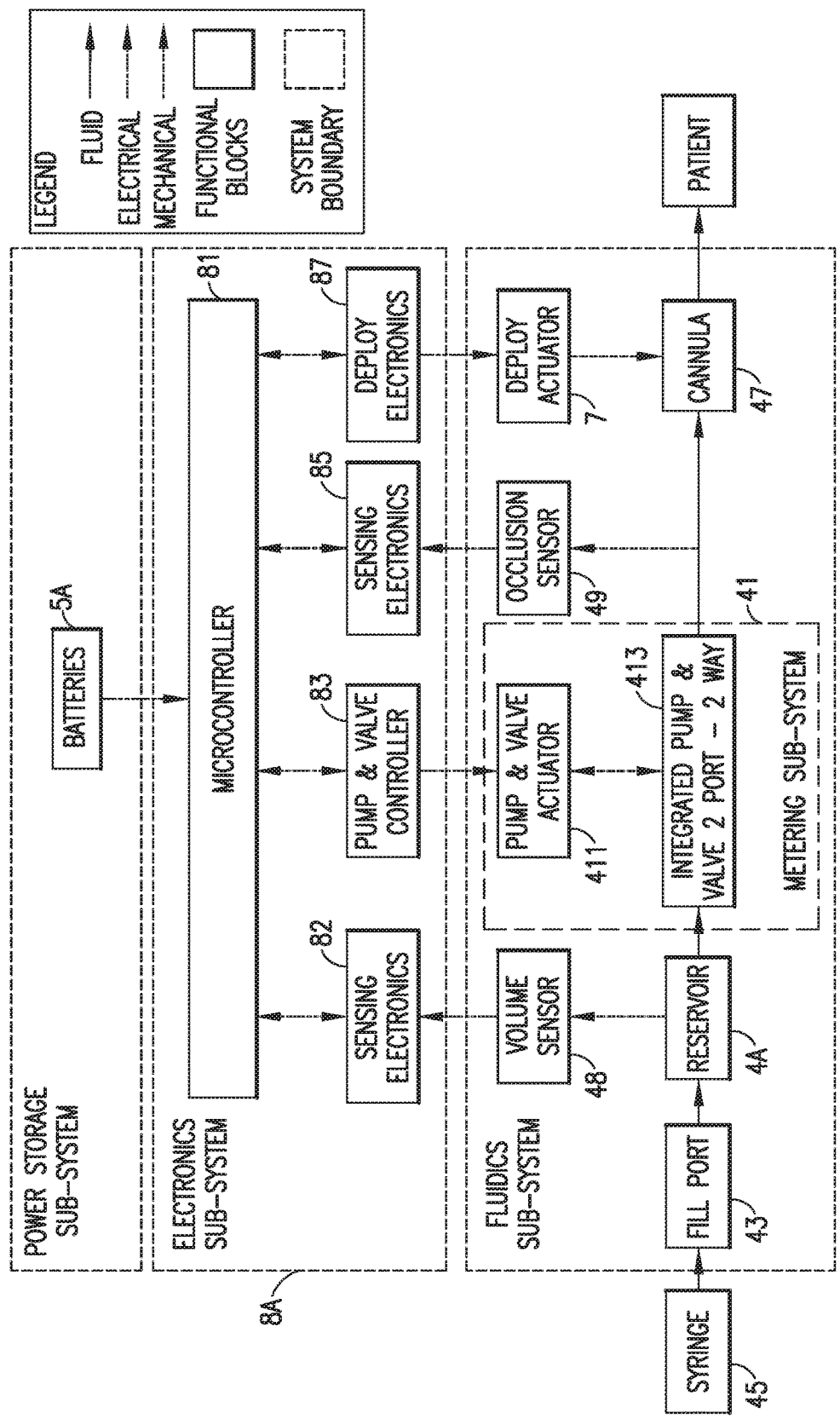
FIG. 4 is a patch-pump fluidic architecture and metering sub-system diagram of the patch pump of FIG. 3.
Figure 5:
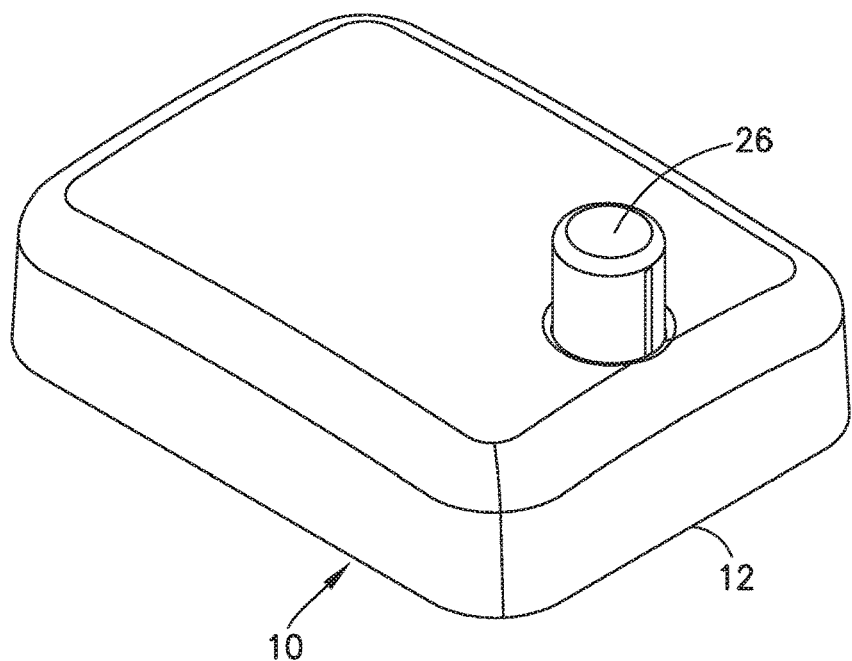
FIG. 5 is a perspective view of the patch pump in one embodiment of the invention.
Figure 6:
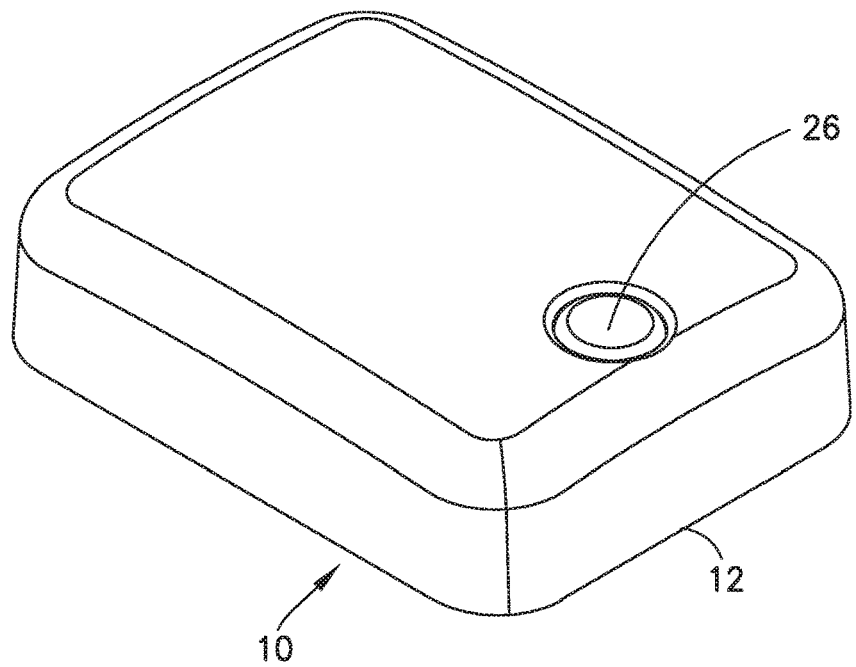
FIG. 6 is a perspective view of the patch pump showing the actuator in the deployed position.

FIG. 4 is a patch-pump fluidic architecture and metering sub-system diagram of the patch pump 1A of FIG. 3. The power storage sub-system for the patch pump 1A includes batteries 5A. The control electronics 8A of the patch pump 1A may include a microcontroller 81, sensing electronics 82, pump and valve controller 83, sensing electronics 85, and deployment electronics 87 that control the actuation of the patch pump 1A. The patch pump 1A includes a fluidics sub-system that may include a reservoir 4A, volume sensor 48 for the reservoir 4A, a reservoir fill port 43 for receiving a refill syringe 45 to refill the reservoir 4A. The fluidics sub-system may include a metering system comprising a pump and valve actuator 411 and an integrated pump and valve mechanism 413. The fluidics sub-system may further include an occlusion sensor, a deploy actuator, as well as the cannula 47 for insertion into an infusion site on the user's skin. The architecture for the patch pumps of FIGS. 1 and 2 is the same or similar to that which is illustrated in FIG. 4.

The present invention is directed to a catheter insertion device for use with a patch pump or infusion set. The invention is particularly directed to a catheter insertion device having an actuator that is manually depressed to insert the catheter into the patient and automatically retract the insertion needle from the catheter.

Referring to FIGS. 5-11, a patch pump referred to herein as an infusion set 10 is provided for introducing a drug or pharmaceutical to a patient need thereof. The infusion set of the invention can be for use with insulin injection although other drugs or pharmaceuticals can be used. The infusion set contains suitable dispensing mechanisms, storage containers and metering devices for extended delivery of the drug or pharmaceutical to the patient as known in the art. The invention is further directed to a method of inserting a catheter into a patient using the catheter device.

The insertion device includes a housing 12 having a base 14 with an internal cavity 16 for containing the supply or reservoir and metering mechanisms for controlled delivery of the insulin, drug, pharmaceutical or other medicament to the patient. The catheter insertion device 18 is mounted within the housing 12 and the base 14. In the embodiment shown, the base 14 is constructed to contact the skin of the patient for delivering the insulin, drug, pharmaceutical, or medicament to the patient. In the embodiment shown, the base 14 has a bottom face 20 with an outwardly extending portion 22 having an aperture 24 for a catheter or other delivery device. The outwardly extending portion 22 extends from the bottom face 20 a distance to assist in stretching the surface of the skin of the patient and to assist in penetration of the catheter, cannula and/or needle into the skin of the patient.

The catheter insertion device 18 includes an actuator 26, a delivery device shown as a catheter 28, and an insertion needle 30. In the embodiment of the invention as shown, the delivery device is a flexible catheter 28 as known in the art having a dimension and length suitable for delivering insulin or other drugs and pharmaceuticals through the skin of a patient with minimal discomfort to the patient. Flexible catheters are generally preferred to reduce the discomfort to the patient. In other embodiments, the delivery device can be a rigid cannula or lumen.

Figure 7:
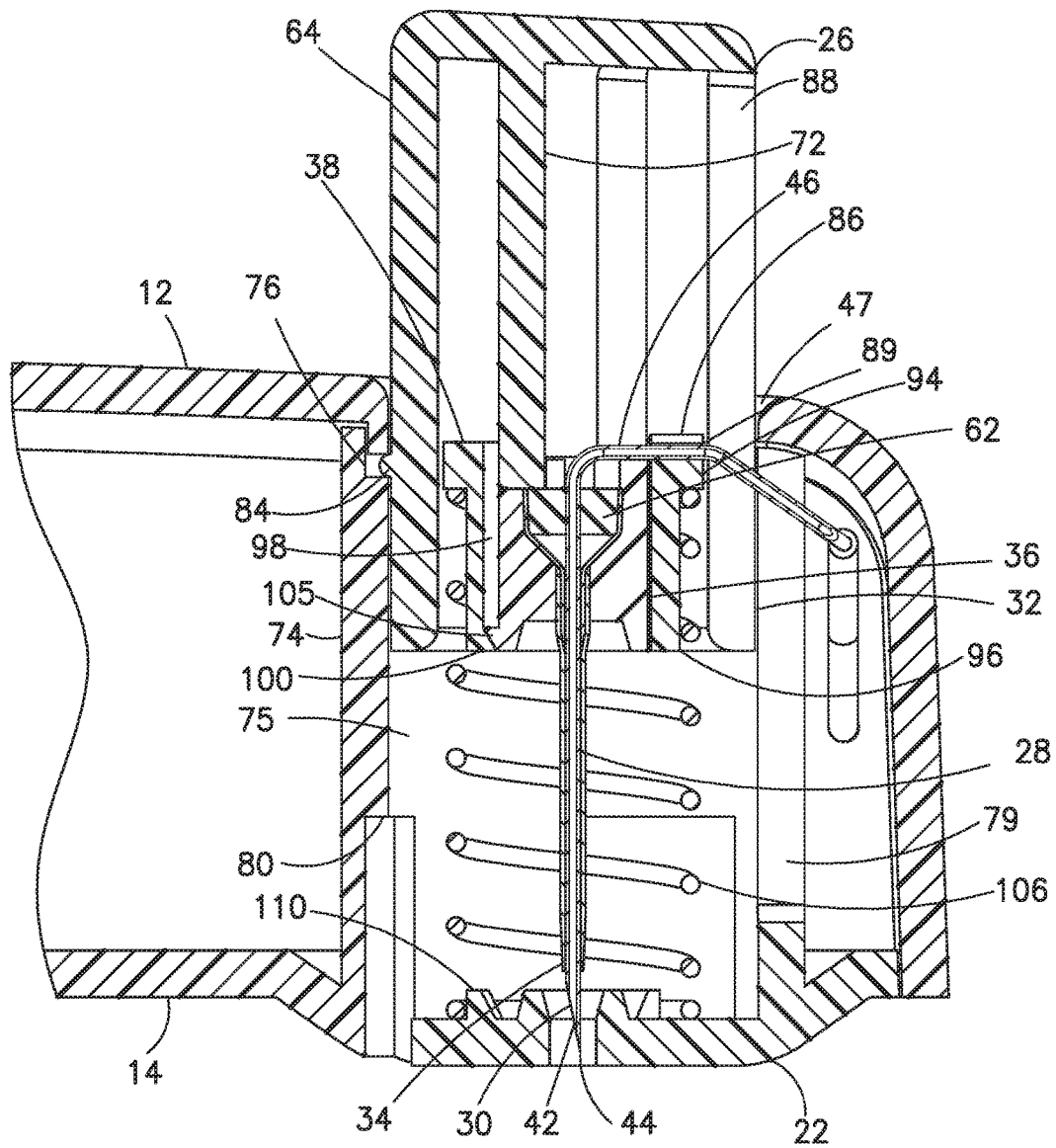
FIG. 7 is a partial cross-sectional view of the catheter insertion device used in the patch pump of FIG. 5.
Figure 8:
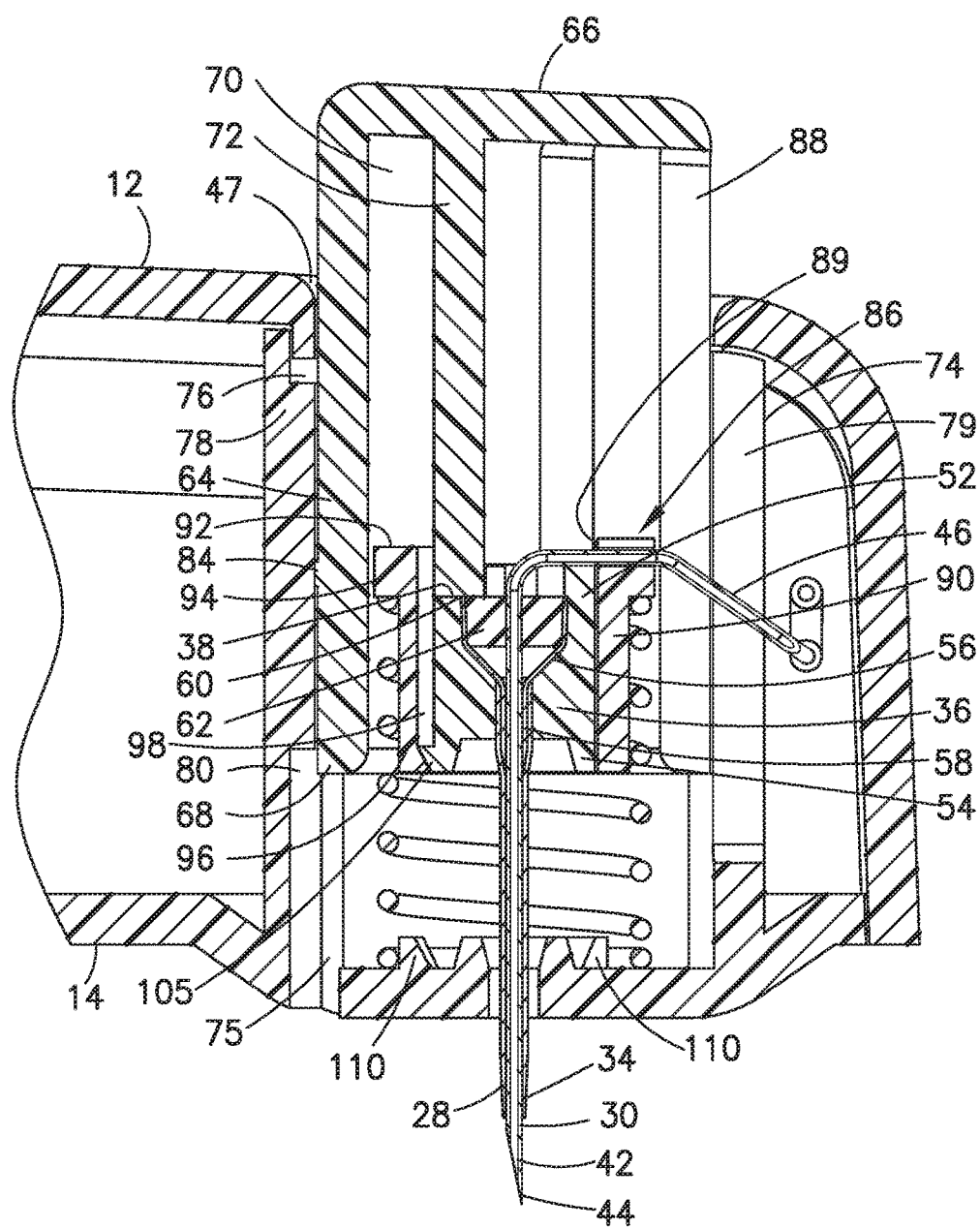
FIG. 8 is a partial cross-sectional view showing the catheter insertion device at the beginning of insertion of the catheter into the patient.

Catheter 28 has a first proximal end 32 and a second distal outer end 34. A fluid passage extends between the ends for delivering the insulin or other drug or pharmaceutical to the patient. In the embodiment shown, first end 32 of catheter 28 is coupled to a catheter hub 36 as shown in FIG. 7. Catheter hub 36 has a substantially cylindrical shape in the embodiment shown for movement within housing 12. Catheter hub 36 is configured for sliding movement within the housing 12. Catheter hub 36 has a passage extending between a first end 52 and a second end 54 having a cavity for receiving a generally funnel shaped member 56 as shown in FIG. 8. Funnel shaped member 56 has a neck 58 inserted into the passage of catheter 28 at the first proximal end 32 by a friction fit or adhesive to couple catheter 28 to catheter hub 36. Funnel shaped member 56 has an upper end 60 with a septum 62.

Insertion needle 30 is received in the passage of catheter 28 and has a length to extend past distal end 34 of catheter 28 as shown in FIGS. 7 and 8. Insertion needle 30 in the embodiment shown is a steel cannula having an internal passage for delivering insulin or other pharmaceutical agents to catheter 28 and to the patient. Insertion needle 30 has a distal end 42 with a sharp tip 44 for penetrating the skin of the patient to assist in inserting catheter 28 into the skin of the patient. Insertion needle 30 passes through septum 62 to provide a fluid tight seal between insertion needle 30 and catheter 28 as known in the art. As shown in FIG. 7, insertion needle 30 has a connecting section 46 connected to the delivery device and fluid supply contained within the housing 12 for delivering the insulin or pharmaceutical agent to the patient. In one embodiment, insertion needle 30 is connected to pump 3 and reservoir 4 as depicted in FIG. 2. As shown in the drawings, insertion needle 30 is mounted for sliding movement within actuator 26 and housing 12 in a substantially linear direction and to slide within the axial passage of catheter 28. In one embodiment as shown, insertion needle 30 travels in a direction substantially perpendicular to the plane of the base 14.

Actuator 26 is in the form of a button or other manually actuated member that is depressed or actuated by the patient during use and insertion of the catheter 28 into the patient. Actuator 26 is movable from a first position shown in FIG. 5 and FIG. 7 where actuator 26 projects outward from the top face of housing 10 to an actuated or deployed position shown in FIGS. 6 and 11 where the outer end of actuator 26 is substantially flush with the top face of housing 10. Actuator 26 in the embodiment shown has a substantially cylindrical configuration and is received within an opening 47 in a top face of housing 12 for sliding movement within opening 48 and housing 10.

In the embodiment shown, actuator 26 has a side wall 64 with a top wall 66 and a bottom distal end 68. Side wall 64 in the embodiment shown has a cylindrical shape and defines an interior cavity 70 for receiving the various components of the actuator assembly 26. In one embodiment of the invention, a member such as a substantially cylindrical shaped sleeve 72 extends from top wall 66 toward distal end 68 of the side wall 64. Sleeve 72 is concentric with side wall 64 and spaced inwardly to define annular cavity 70. In one embodiment, sleeve 72 has a length less than a length of side wall 64 so that the end of the sleeve 72 is spaced from the bottom distal end 68 a distance corresponding substantially to the dimension of catheter hub 36.

In the embodiment shown, a cylindrical wall 74 is provided within housing 12 for defining a passage 75 for receiving actuator 24 and allowing sliding movement of actuator 24 with respect to the housing 12 and base 14. In one embodiment, cylindrical wall 74 is integrally formed with base 12. Cylindrical side wall 74 is provided with a recess 76 at a top end 78 and a recess 80 toward a bottom end at or near base 14. A longitudinal slot 79 is formed in side wall 74 to receive the connecting portion 46 of insertion needle 30 and allow linear or sliding movement of insertion needle 30 within side wall 74. An outwardly extending detent 84 projects outwardly from side wall 64 and has a dimension to be received in the respective recess 80 and recess 76. In other embodiments, detent 84 can be on side wall 74 and complementing first and second recesses can be on actuator 24.

Insertion needle 30 is coupled to a needle carrier 86. In the embodiment shown, needle carrier 86 is received in annular cavity 70 of actuator 26. In the embodiment shown, needle carrier 86 has a cylindrical or annular shape forming a sleeve that slides within annular cavity 70 of actuator 26 around sleeve 72. As shown in FIG. 7, insertion needle 30 extends through an aperture or slot 89 in a side wall 90 of the carrier 86 so that insertion needle 30 is movable with movement of needle carrier 86. In the embodiment shown, needle 30 is coupled to carrier 86 by a friction fit in slot 89. Side wall 64 of actuator 26 has a longitudinal slot 88 to enable needle carrier 86 and insertion needle 30 to slide within actuator 26. Sleeve 72 also has a longitudinal slot 91 aligned with slot 88 to allow sliding movement of insertion needle 30.

Figure 10:
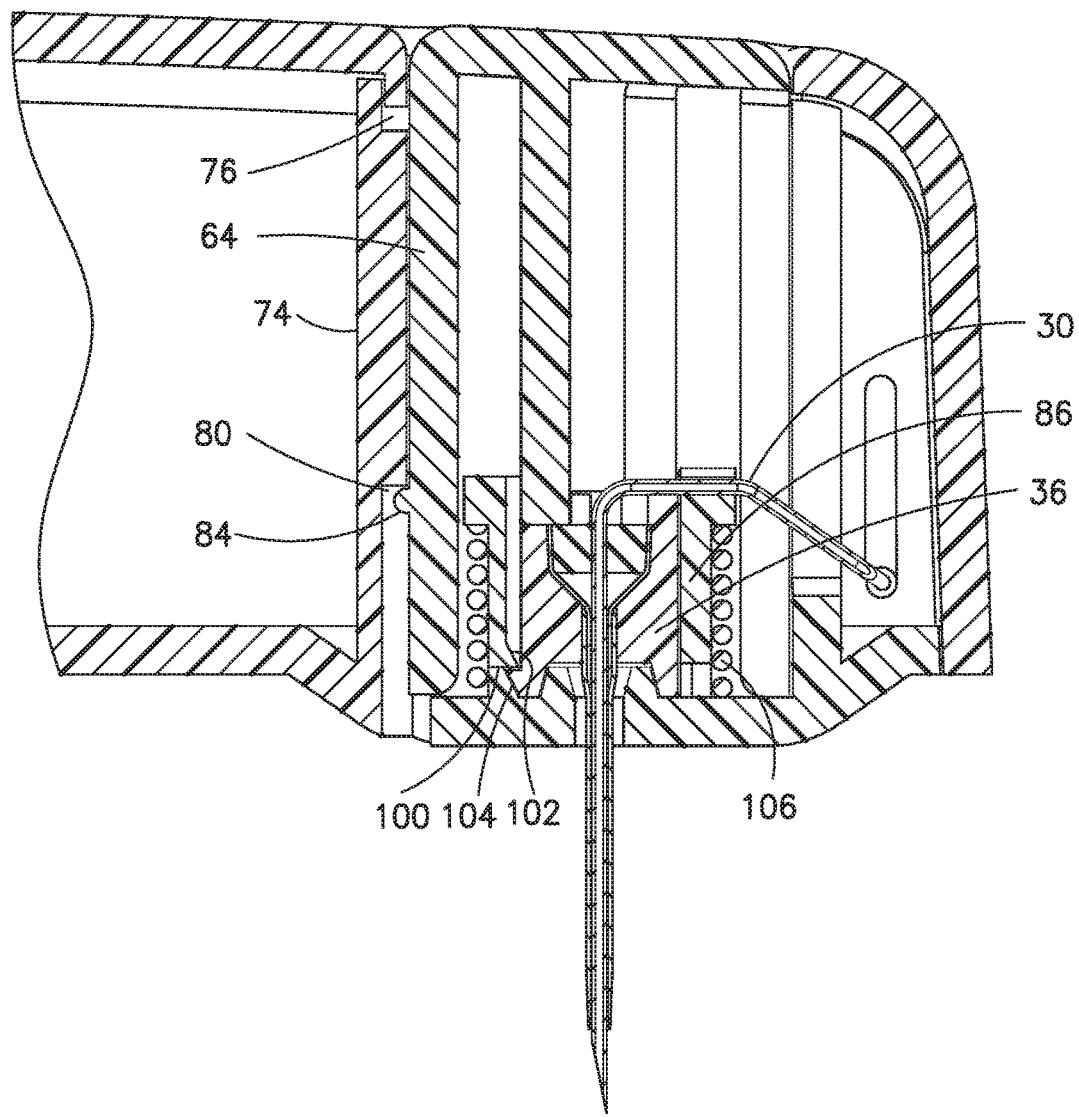
FIG. 10 is a cross-sectional view showing the catheter insertion device with the insertion needle in the extended position.

Needle carrier 86 has a cylindrical side wall 90 with the top end 92 having an outwardly extending flange 94 and a bottom end 96. An inner surface of cylindrical side wall 90 has at least one inwardly extending detent 100 at bottom end 96. In one embodiment, three or four detents 100 are spaced around carrier 86 to effectively engage catheter hub 36. In the embodiment shown, each detent 100 has an inclined face 102 for mating with the inclined face 104 of detent 105 extending outwardly from the bottom end of catheter hub 36 as shown in FIG. 10.

Figure 11:
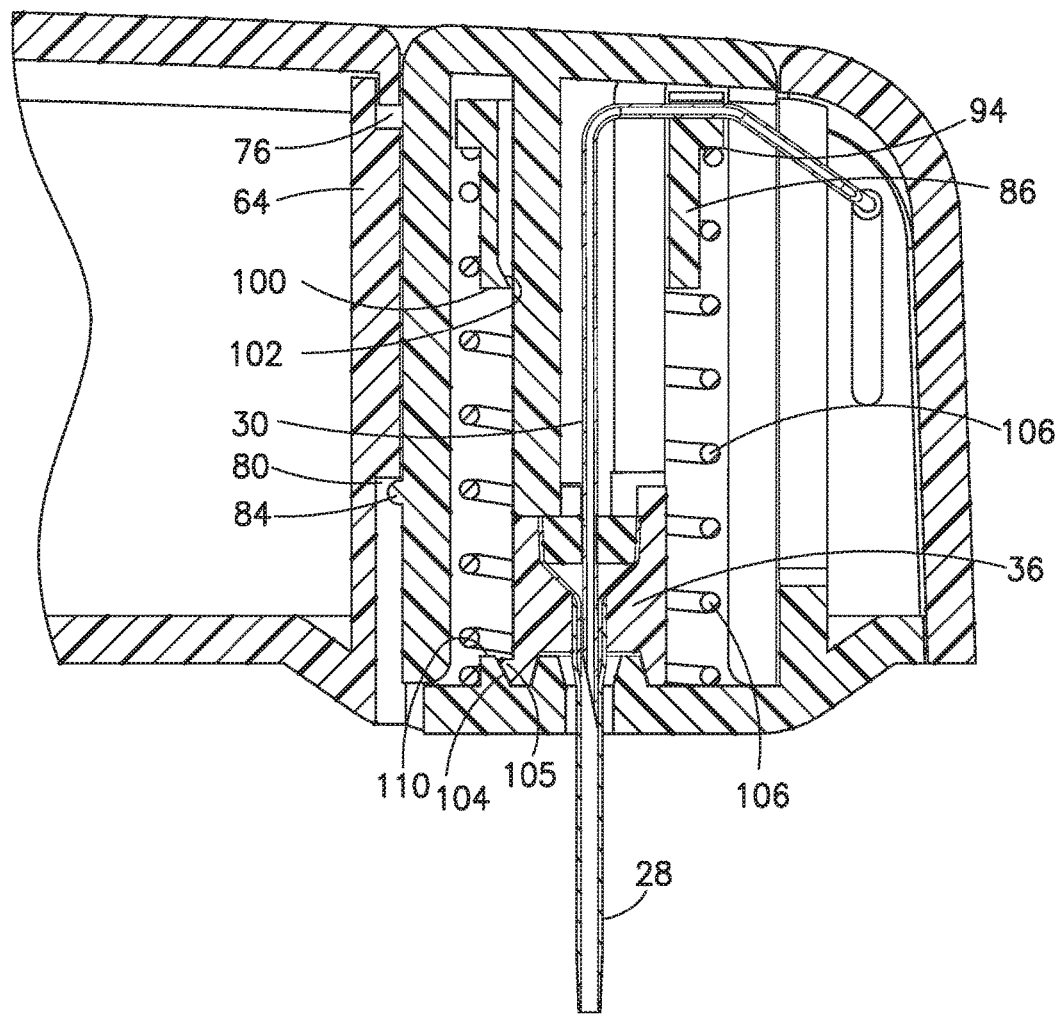
FIG. 11 is a cross-sectional view showing the catheter in the extended position and the insertion needle in the retracted position.

A biasing member in the form of a spring 106 is positioned between needle carrier 86 and base 14 to bias needle carrier 86 to a retracted position shown in FIG. 7 and FIG. 11. Spring 106 in the embodiment shown is provided within annular cavity 70 of cylindrical side wall 74 and extends between the base 14 and flange 94 to bias needle carrier 86 in a retracting direction away from the base 14. Spring 106 initially biases actuator 24 to the first position shown in FIG. 7 by the connection between carrier 86 and actuator 24.

As shown in FIG. 7, needle carrier 86 engages and is removably coupled to the bottom end of actuator 26 via the catheter hub 36 so that a downward movement of actuator 26 moves catheter hub 36, needle carrier 86 and insertion needle 36 in a downward direction against the biasing force of spring 106 to compress spring 106. An actuating force is applied in a downward direction by the user on actuator 26 to disengage and separate detent 84 on the side wall 64 of actuator 26 from recess 76 and enable actuator 26 to slide toward base 14 as shown in FIG. 8. Detent 84 on the side wall 64 of actuator 26 engages recess 76 to require a predetermined force to separate detent 84 from recess 76 where the force required is greater than the force required to slide actuator 26 along the side wall 64 as shown in FIG. 8. The detent 84 in side wall 64 of actuator 26 couples with recess 76 and form a snap connection which requires a predetermined force to break free which is greater than the force required to compress spring 106. In this manner, and actuating force is applied to actuator 26 to separate the detent 84 from recess 76 which then allows a rapid and complete sliding movement of actuator 26 to the actuated and deployed position shown in FIGS. 8-10.

Figure 9:
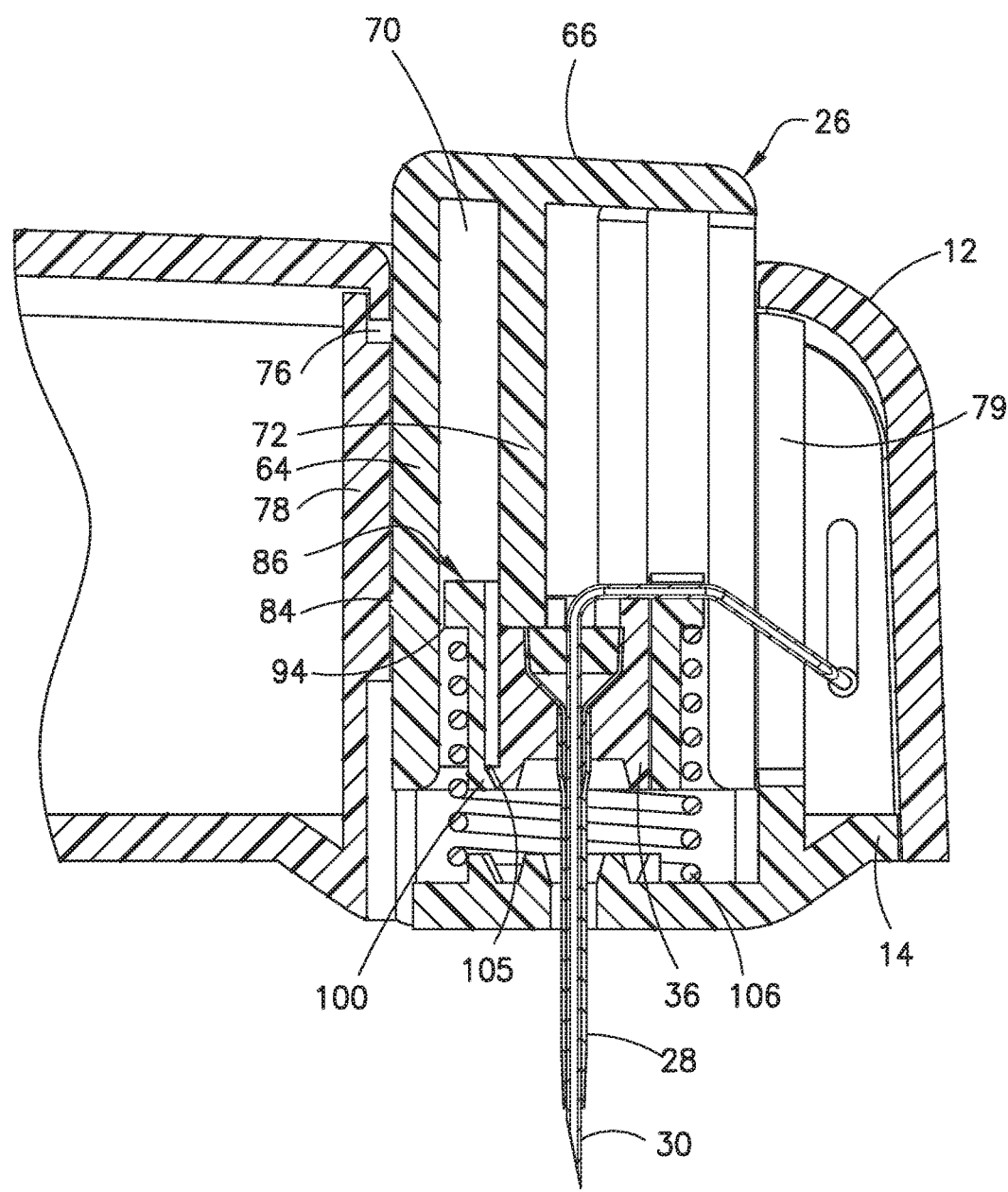
FIG. 9 is a partial cross-sectional view showing the catheter insertion device during insertion of the catheter into the patient.

Base 14 includes at least one detent 110 extending in a generally upward direction and positioned to contact distal end of detents 100 on needle carrier 86. Referring to FIG. 9, the downward movement of actuator 26 carries catheter hub 36 and needle carrier 86 against the compression force of spring 106 to move catheter 28 and insertion needle 30 to the extended position shown in FIG. 9 for penetrating the skin of the patient. As shown in FIG. 10, detent 110 on base 14 contacts distal end 96 of needle carrier 86 so that the further downward movement of actuator 26 pushes catheter hub 36 further toward the base 14 causing the inclined surfaces of the respective detent 105 on catheter hub 36 and detent 100 on needle carrier 86 to separate along the respective inclined surfaces 102 and 104, thereby disengaging needle carrier 86 from catheter hub 36 as shown in FIG. 10. Once the detents 100 and 105 separate and disengage as shown in FIG. 10, spring 106 biases needle carrier 86 away from base 14 and catheter hub 36 to retract insertion needle 30 into catheter 28 as shown in FIG. 11. Detent 100 then slides along slot 98 formed on the outer surface of catheter hub 36.

During the downward movement, catheter hub 36 and catheter 28 slide in a downward direction further than the position of insertion needle 30 as a result of needle carrier 86 contacting detent 110 on base 14. As catheter hub 36 slides past needle carrier 86, the detents 100 and 105 separate to separate catheter hub 36 from needle carrier 86. The biasing force of spring 106 then retracts needle carrier 86 and insertion needle 30 into housing 12 and into actuator 26 to the position shown in FIG. 11. A pharmaceutical agent is then supplied through the passage of insertion needle 30 from a fluid supply and metering device to deliver the pharmaceutical agent to catheter 28 now positioned in the skin of the patient to deliver the pharmaceutical agent. The detent 84 on the actuator 26 couples with the recess 80 to retain actuator 26 and catheter 28 in the deployed position where the catheter extends from the housing 12.

In the drawings, a single detent 100 on needle carrier 86 and a single detent 105 on catheter hub 36 are shown. It will be understood that one or more complementing detents can be provided for coupling catheter hub 36 and needle carrier 86 together. In one embodiment, three uniformly spaced apart detents are formed on the catheter hub and needle carrier for removably coupling the needle carrier to the catheter hub. In one embodiment, detent 100 on needle carrier 86 can be a flexible leg or tab that is able to deflect outwardly by the opposing inclined surfaces 102 and 104.

In the embodiment shown, needle carrier 86 is connected to actuator 26 by catheter hub 36 whereby separation of needle carrier 86 from catheter hub 36 enables spring 106 to automatically retract the needle carrier 86 and insertion needle 30 into actuator 26 as shown in FIG. 11. In other embodiments, needle carrier 86 can be removably coupled to the other parts of the assembly that enable spring 106 to retract an insertion needle 30 after deployment of catheter 28. In one embodiment, needle carrier 86 can have a detent that extends outwardly from the side wall and engages a complementing recess in the inner face of side wall 64 positioned toward the distal end to removably couple needle carrier 86 to the distal end of actuator 26. The detent 110 on base 14 can be positioned to contact the end of needle carrier 86 to separate the detent from the corresponding recess, whereby spring 106 retracts insertion needle 30 and needle carrier 86 in a similar manner to the embodiment illustrated.

While various embodiments have been shown and described, it will be understood by those skilled in the art that various changes and modifications can be made without departing from the scope of the invention as defined in the appended claims.

The invention claimed is:

1. A catheter insertion device comprising:
a housing having a base:
a catheter coupled to a catheter hub positioned in said housing and movable between a first catheter position and a second catheter position with respect to said base;
a needle carrier having an introducer needle, said introducer needle received within said catheter and movable between a first introducer needle position and a second introducer needle position with respect to said base and catheter, said catheter hub positioned within said needle carrier when said catheter hub is in said first catheter position; and
an actuator slidable in said housing for actuating said catheter insertion device, said actuator directly engaging said catheter hub and moving said catheter hub and introducer needle from said first catheter position and said first introducer needle position where said catheter and introducer needle are retracted within said housing, and said second catheter position and said second introducer needle position where said catheter and introducer needle extend from said base, and where said needle carrier and introducer needle automatically retract into said actuator when said catheter and said introducer needle reach said second catheter position and said second introducer needle position.

2. The device of claim 1, further comprising
a projection on said actuator received in a first recess in said housing, said projection on said actuator and said first recess requiring a predetermined force applied to said actuator to move said actuator from a first position to a second position, and a second recess on said housing receiving said projection on said actuator when said actuator is in said second position to retain said actuator in said second position.

3. The device of claim 1, wherein
said actuator includes a sleeve and where said needle carrier is slidably received on said sleeve of said actuator, said needle carrier being releasably coupled to said catheter hub and configured for separating from said actuator when said catheter and introducer needle move to said second catheter position and said second introducer needle position to retract said introducer needle into said actuator and slide the needle carrier on said sleeve introducer needle position.

4. The device of claim 3, further comprising
a spring to spring bias said needle carrier and said introducer needle to said first introducer needle position on said sleeve of said actuator, where said spring is in an extended position when said actuator and needle carrier are in said first introducer needle position and compressed when said actuator and needle carrier are in said second introducer needle position.

5. The device of claim 4, wherein
said needle carrier has an annular shape having a distal end with a needle carrier detent projecting radially inward from said needle carrier and releasably coupled to an outwardly extending catheter hub detent on said catheter hub, whereby moving said actuator from said first position to said second position moves said catheter hub and needle carrier to said second catheter position and said second introducer needle position, and
where said base has a base detent to engage said needle carrier detent of said needle carrier when said actuator is in said second position to separate said needle carrier from said catheter hub to retract needle carrier and said introducer needle with respect to said catheter hub.

6. The device of claim 3, wherein
said actuator has a side wall surrounding said sleeve of said actuator, said needle carrier is a sleeve slidably received on said sleeve in said actuator, and said catheter hub is received in said sleeve of said needle carrier in said first catheter position.

7. The device of claim 1, wherein said actuator has a sleeve surrounded by a side wall, said sleeve of said actuator directly engaging said catheter hub to move said catheter hub, said needle carrier having an annular shape and slideably received on said sleeve of said actuator.

8. The device of claim 7, wherein said side wall and said sleeve of said actuator have a longitudinal slot, and where said introducer needle has a connecting portion connected to a fluid supply and where said connecting portion extends transversely through said longitudinal slots and slides longitudinally through said longitudinal slots with sliding movement of said needle carrier relative to said actuator.

9. A catheter insertion device comprising:
a housing having a base with a base detent extending from said base;
a catheter hub having a catheter movable between a first catheter position and a second catheter position with respect to said base;
a needle carrier having an introducer needle within said catheter and movable between a first introducer needle position and a second introducer needle position with respect to said base, where said catheter hub is slidably received within said needle carrier and where said needle carrier includes a needle carrier detent releasably coupled to said catheter hub;
an actuator movable with respect to said base, said catheter hub and needle carrier being movable with said actuator, and said needle carrier being slidably received in said actuator, said actuator being movable between a first position where said catheter hub and needle carrier are in catheter position and said first introducer needle position within the base and a second position where said catheter hub and needle carrier are in catheter position and said second introducer needle position, said needle carrier detent on said needle carrier engaging said base detent on said base to release said needle carrier from said catheter hub and retract said needle carrier and introducer needle; and
a spring surrounding said catheter hub and said needle carrier to bias said needle carrier to said first introducer needle position, said spring extending between said base and said needle carrier, said spring being in an extended position when said needle carrier is in said first introducer needle position and a compressed position when said needle carrier is in said second introducer needle position.

10. The device of claim 9, wherein
said actuator has an outer surface with an outwardly extending projection received in a first recess in said housing to require a predetermined force to move said actuator from a first position to a second position, and said housing having a second recess receiving said outwardly extending projection when said actuator is in said second position to retain said actuator in said second position.

11. The device of claim 10, wherein
said catheter hub has a first end directly contacting said actuator and a second end, said second end of said catheter hub having an outwardly extending catheter hub detent releasably coupled to said needle carrier detent on said needle carrier.

12. The device of claim 11, wherein
said needle carrier forms a sleeve surrounding said catheter hub and being slidable with respect to said catheter hub, and
said spring positioned between said needle carrier and said base to bias said needle carrier to said first introducer needle position by separation of said needle carrier from said catheter hub.

13. The device of claim 9, wherein
said actuator has a side wall with a longitudinal slot, and where said introducer needle has a connecting portion connected to a fluid supply and where said connecting portion extends transversely through said longitudinal slot in said side wall of said actuator and slides longitudinally in said slot when said needle carrier slides from said second introducer needle position to said first introducer needle position.

14. The device of claim 9, wherein
said introducer needle is a cannula connected to a fluid supply for supplying a pharmaceutical agent to said catheter.

15. A catheter insertion device comprising:
a housing having a base;
an actuator coupled to said housing and being movable between a first position and a second position, said actuator having a side wall and a sleeve within said outer side wall;
a catheter hub within said actuator and having a flexible catheter and being movable between a first catheter position disposed within said housing and a second catheter position extending from said housing when said actuator is in said second position, and where said sleeve of said actuator directly engages an end of said catheter hub;
a needle carrier slidably received on said sleeve of said actuator and slidable between a first introducer needle position with respect to said actuator and catheter hub, and a second introducer needle position, and where said needle carrier is releasably coupled to said catheter hub; and
an introducer needle received in said sleeve of said actuator and said flexible catheter and coupled to said needle carrier, where said needle carrier, introducer needle and catheter are movable to said second catheter position and said second introducer needle position by movement of said actuator, and where said needle carrier separates from said catheter hub when said catheter hub contacts said base of said housing at said second introducer needle position to retract said needle carrier and introducer needle into said actuator.

16. The device of claim 15, further comprising
a spring positioned between said needle carrier and said base to bias said needle carrier to the first introducer needle position.

17. The device of claim 16, wherein
said catheter hub has an outwardly extending catheter hub detent at a distal end thereof projecting toward said needle carrier, and said needle carrier has an inwardly extending needle carrier detent to removably couple with outwardly extending catheter hub detent on said catheter hub.

18. The device of claim 17, wherein
said base has a base detent extending toward said needle carrier and positioned to contact said needle carrier detent of said needle carrier when said needle carrier is moved to said second introducer needle assembly.

19. The device of claim 18, wherein
a distal end of said needle carrier contacts said base detent on said base before said catheter hub and actuator are in the second catheter position and the second position respectively to separate said needle carrier from said catheter hub.

20. The device of claim 15, wherein said side wall of said actuator includes a longitudinal slot and where a connecting portion of said introducer needle slides longitudinally through said longitudinal slot.

* * * * *